(12) United States Patent
Denninghoff et al.

(10) Patent No.: US 8,706,178 B2
(45) Date of Patent: Apr. 22, 2014

(54) METHOD AND DEVICE FOR DETERMINING OXYGEN SATURATION OF HEMOGLOBIN, FOR DETERMINING HEMATOCRIT OF BLOOD, AND/OR FOR DETECTING MACULAR DEGENERATION

(75) Inventors: Kurt R. Denninghoff, Tucson, AZ (US); Lloyd W. Hillman, Hampton Cove, AL (US); Sharon Hillman, legal representative, Hampton Cove, AL (US)

(73) Assignees: UAB Research Foundation, Birmingham, AL (US); The University of Alabama in Huntsville, Huntsville, AL (US)

( * ) Notice: Subject to any disclaimer, the term of this patent is extended or adjusted under 35 U.S.C. 154(b) by 1132 days.

(21) Appl. No.: 11/913,372

(22) PCT Filed: May 2, 2006

(86) PCT No.: PCT/US2006/016883
§ 371 (c)(1),
(2), (4) Date: Jul. 29, 2009

(87) PCT Pub. No.: WO2006/119314
PCT Pub. Date: Nov. 9, 2006

(65) Prior Publication Data
US 2010/0030042 A1 Feb. 4, 2010

Related U.S. Application Data

(60) Provisional application No. 60/677,681, filed on May 4, 2005.

(51) Int. Cl.
*A61B 5/1455* (2006.01)

(52) U.S. Cl.
USPC .................................................. 600/323

(58) Field of Classification Search
USPC ............... 600/310, 322, 323, 331, 332, 339; 356/39, 40, 41; 422/82.05
See application file for complete search history.

(56) References Cited

U.S. PATENT DOCUMENTS

| | | | |
|---|---|---|---|
| 5,318,022 A * | 6/1994 | Taboada et al. | 600/323 |
| 5,817,144 A * | 10/1998 | Gregory | 607/89 |
| 6,859,658 B1 * | 2/2005 | Krug | 600/323 |
| 8,126,527 B2 * | 2/2012 | Marcinek et al. | 600/322 |
| 2003/0139667 A1 | 7/2003 | Hewko et al. | |

OTHER PUBLICATIONS

PCT Search Report and Written Opinion for PCT/US06/16883 dated Jun. 4, 2008.

* cited by examiner

*Primary Examiner* — Eric Winakur
(74) *Attorney, Agent, or Firm* — Alston & Bird LLP

(57) ABSTRACT

A method and device for accurately determining oxygen saturation of hemoglobin by the measurement of the optical density of a sample, such as a blood vessel, in response to illumination by light having at least three wavelengths ($\lambda 1, \lambda 2, \lambda 3, \ldots$) within a range of about 460 nm to about 523 nm. The hematocrit of a sample may be determined from optical density measurements at the three or more wavelengths in conjunction with a known path length. The device may be an intravenous or intra-arterial fiber optic catheter used to deliver the interrogating light signal to the blood and to detect the reflected signal. A method and device of determining the thickness of the retinal well using spectroscopic information are also disclosed.

3 Claims, 3 Drawing Sheets

METHOD AND DEVICE FOR DETERMINING OXYGEN SATURATION OF HEMOGLOBIN, FOR DETERMINING HEMATOCRIT OF BLOOD, AND/OR FOR DETECTING MACULAR DEGENERATION

CROSS REFERENCE TO RELATED APPLICATIONS

This application is a national phase entry of International Application No. PCT/US2006/016883 filed May 2, 2006, which claims priority to U.S. Provisional Application No. 60/677,681, filed May 4, 2005.

BACKGROUND OF THE INVENTION

One aspect of the invention relates to a method and device for determining the oxygen saturation of blood and, in particular, intra-cellular or extra-cellular hemoglobin with spectroscopic analysis. A further aspect of the invention relates to a method of detecting failed autoregulation from spectroscopic analysis of a retina including retinal vessels. Another aspect of the invention relates to a method and device for determining the hematocrit of blood using information derived from spectroscopic analysis and or macular degeneration using information derived from spectroscopic analysis of a retina including retinal vessels.

A variety of spectroscopic oximetry techniques have been proposed for monitoring the blood oxygen saturation and blood oxygen content in retinal vessels. By successfully monitoring the blood oxygen saturation, the arteriovenous oxygen difference can be determined as described by U.S. Pat. No. 5,308,919 to Thomas E. Minnich, U.S. Pat. No. 5,776,060 to Matthew H. Smith, et al., and U.S. Pat. No. 5,935,076 to Matthew H. Smith, et al. Based upon the arteriovenous oxygen difference, the cardiac output of a subject can be approximated in order to assist in post-operative monitoring and the management of critically ill patients. By monitoring the blood oxygen saturation, the loss of blood can be detected, and the rate and quantity of blood loss over time can be estimated as described by U.S. Pat. No. 5,119,814 to Thomas E. Minnich.

In addition to the variety of invasive techniques that require blood to be drawn, oftentimes repeatedly, from a patient, a number of non-invasive spectroscopic oximetry techniques have been proposed and attempted with the intent to measure the blood oxygen saturation of a patient without requiring blood to be drawn from the patient. For example, a number of noninvasive spectroscopic oximetry techniques have been proposed which attempt to measure the blood oxygen saturation of a patient based upon the transmittance of the blood within a retinal vessel, such as a retinal vein or a retinal artery. For example, U.S. Pat. Nos. 5,776,060 and 5,935,076 describe techniques for measuring the oxygen saturation of blood within a retinal vessel by illuminating the retinal vessel with light having a combination of wavelengths and then measuring the transmittance of the blood within the retinal vessel in response to the illumination at each of the selected wavelengths. Based upon the respective transmittance of the blood within the retinal vessel that is measured at each of the selected wavelengths, the oxygen saturation of the blood within the retinal vessel can be approximated. The contents of U.S. Pat. Nos. 5,776,060 and 5,935,076 are hereby incorporated by reference in their entirety.

As will be apparent, the light with which a retinal vessel is illuminated can be reflected and transmitted in a variety of different manners. For example, some of the light will be immediately reflected by the retinal vessel, while other portions of the light will be backscattered by the red blood cells within the retinal vessel. Other portions of the light, termed "double pass light", will pass through the retinal vessel, be reflected from the retinal and/or choroidal layers and again pass through the retinal vessel, thereby traversing the retinal vessel twice. Further, some portion of the light, termed "single pass light", will pass through the retinal vessel, diffuse laterally through the retinal and/or choroidal layers and then exit the pupil without again traversing the retinal vessel.

Regardless of the particular paths traveled by the optical signals, the optical signals that return from the eye are collected by a detector and then an associated processing element, such as a microprocessor, a personal computer or the like, which can determine the blood oxygen saturation within the retinal vessel based upon the light that is returned. In order to determine the blood oxygen saturation, techniques have been developed to account for light that has been reflected and/or transmitted in each of the various manners described above. As a result of the variety of different ways in which light can be reflected and/or transmitted, however, the equations that must be solved to determine the blood oxygen saturation within the retinal vessel are quite complicated and may reduce the accuracy with which the blood oxygen saturation can be determined. Further, the equations used require knowledge of a large number of variables, such as hemoglobin concentration within the blood and path length, which must be determined prior to use of the equations.

It is desired to provide a spectroscopic method to non-invasively determine the oxygen saturation of blood in a living organism, where the method is highly calibrated and accurate relative to prior art spectroscopic techniques (fiber optic catheters are calibrated to +−9% Saturation). It is further desired to provide a spectroscopic method that may be used to accurately determine oxygen saturation of blood that requires a minimum of independent variables and does not vary with such factors as pH, red blood cell concentration, hemoglobin concentration and path length of the interrogating light. It is also desired to use data obtained by spectroscopic analysis to determine hematocrit of a sample, and to determine the thickness of one or more retinal layers for the diagnosis of macular degeneration and other retinal diseases.

BRIEF SUMMARY OF THE INVENTION

According to a first embodiment, a method and device are provided for accurately determining oxygen saturation of blood and, in particular, intra-cellular or extracellular hemoglobin by the measurement of the optical density of a sample, such as a blood vessel, in response to illumination with light of at least three wavelengths ($\lambda_1, \lambda_2, \lambda_3, \ldots$) within a range of about 460 nm to about 523 nm. The resulting optical density measurements determined from illumination with multiple wavelengths of light in the 460 nm to 523 nm range exhibit a local minima that, in turn, has a linear relationship to oxygen saturation. The method and device of this embodiment provide oxygen saturation measurements of increased accuracy over prior art techniques because it is not dependent upon pH, hematocrit, hemoglobin concentration or path length of the interrogating light, variables which introduced significant error in calculations of the past.

According to another embodiment of the invention, hematocrit of a sample may be determined from optical density measurements at the three or more wavelengths in conjunction with a known path length. A device may be embodied in different forms, allowing for determination of the hematocrit as well as the oxygen saturation. One such embodiment would include an intravenous or intra-arterial fiber optic catheter used to deliver the interrogating light signal to the blood and to detect the transmitted signal.

According to a further embodiment of the invention, the thickness of retinal layers may be measured using information within the laterally scattered light detected during spectroscopic analysis. While light of various wavelengths may be utilized to obtain the information from which the thickness measurement may be made, one advantageous embodiment utilizes the light emitted by a red targeting laser, such that the red laser serves the dual purpose of visibly illuminating the target and providing information regarding retinal thickness. The measured thickness may be compared to standard thicknesses in order to determine if the retinal layer(s) is abnormal. A practical application of this test is the detection of macular degeneration.

BRIEF DESCRIPTION OF THE SEVERAL VIEWS OF THE DRAWINGS

Figure 1:
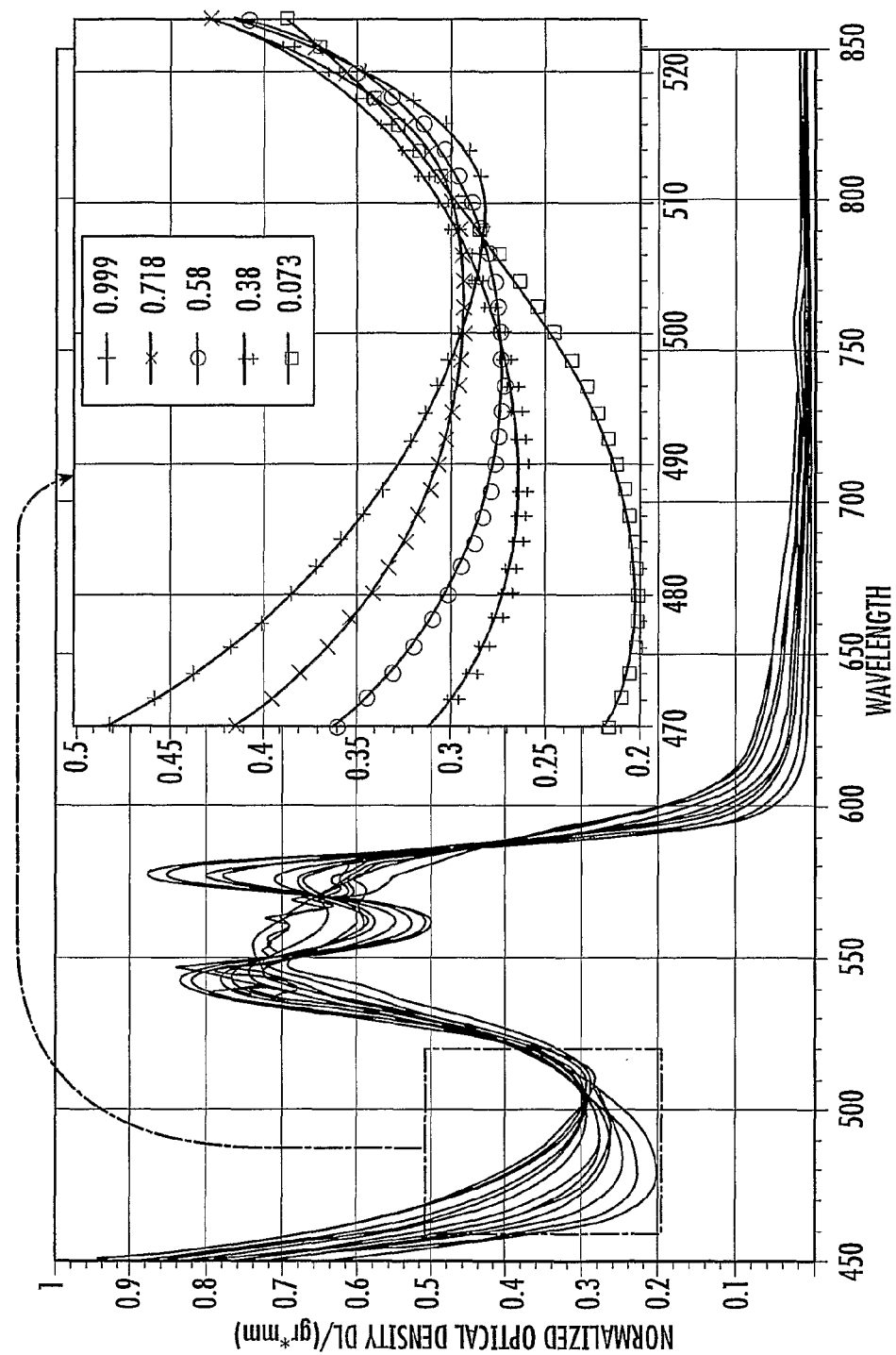
Figure 2:
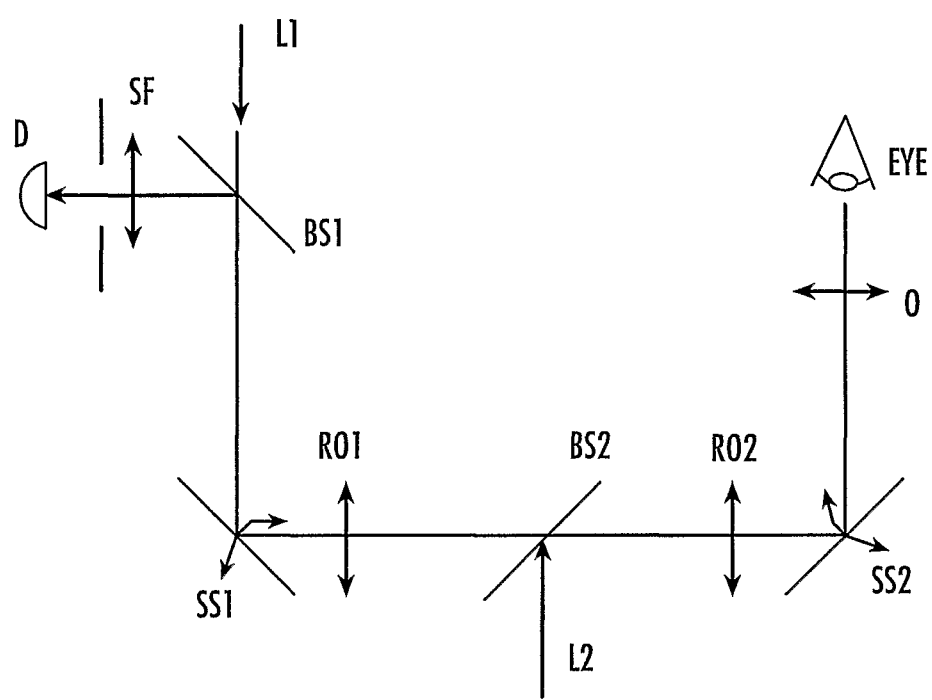
Figure 3:
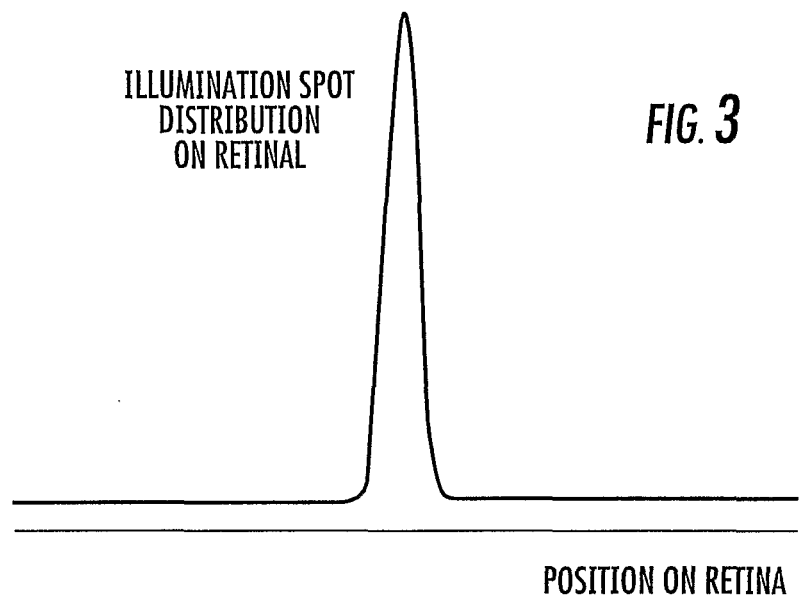
Figure 4:
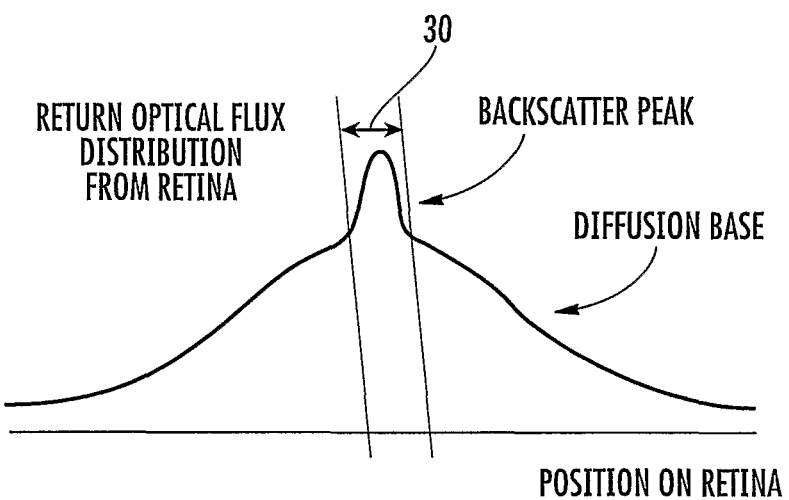

Having thus described the invention in general terms, reference will now be made to the accompanying drawings, which are not necessarily drawn to scale, and wherein:

FIG. 1 is a graph of the optical density of 16 hemoglobin samples measured at a wavelength ranging from 450 nm to 850 nm;

FIG. 1*a* is an expanded portion of FIG. 1 showing minima of the measured spectra in the wavelength range of from 460 nm to 523 nm;

FIG. 2 is an exemplary schematic showing a spectroscopic setup for use in one embodiment of this invention;

FIG. 3 is a graph of an exemplary illuminance vs. retinal position distribution; and FIG. 4 is a graph of an exemplary detected return optical flux vs. retinal position distribution.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

According to one embodiment of the invention, oxygen saturation of a blood or hemoglobin sample may be accurately determined by measurement of optical density at three or more wavelengths. This three-wavelength minimum oxygen saturation determination technique was developed after exploring the oxygen saturation of hemoglobin relative to the four potential oxygen binding sites on each hemoglobin molecule. Oximetry techniques and the underlying equations of the past have generally assumed that there are only two forms of hemoglobin, deoxyhemoglobin and oxyhemoglobin. However, hemoglobin exists as a four molecule grouping that binds to oxygen cooperatively with at least 10 different intermediate combinations of oxygen, hemoglobin and macromolecular structures. Thus, some prior techniques have oversimplified the forms of hemoglobin, thereby producing results that may be somewhat inaccurate. A more detailed explanation of the reasons for the increased accuracy of this method over oxygen saturation determination methods of the prior art is provided in Example 3 below.

Referring to FIG. 1, exemplary determinations of oxygen saturation are shown in order to illustrate this aspect of the invented method. Blood samples, each having a known oxygen saturation, were illuminated with a range of wavelengths from 450 nm to 850 nm at 2 nm increments. The intensity of the return signals was measured and the corresponding optical density was determined as described below. The measured signals were normalized with a value of 1.0 corresponding to the largest optical density, that is, the optical density of a fully saturated hemoglobin sample at 450 nm. Samples of various oxygen saturations were used, from solutions having virtually no oxygen (0.073) to virtually fully oxygenated (0.999).

The optical density of the different hemoglobin samples all have a local minimum somewhere in the range of 460 to 523 nm, depending on the particular characteristics of the sample. Sixteen separate samples are shown in FIG. 1, with details of five of the samples shown in FIG. 1*a*. It has been found that the minima of the parabolic curve between about 460 and 523 nm moves laterally, i.e. the minima corresponds to varying wavelengths, depending on the hemoglobin oxygen saturation of the sample being measured. Most other regions of the measured spectra vary in amplitude or only slightly laterally. The optical density minimum between 460 to 523 nm varies by the greatest amount of the various points of inflection so as to provide the best ability to discriminate between solutions of different degrees of oxyhemoglobin and deoxyhemoglobin.

The minima of any given sample may be mathematically determined by measuring the optical density with three or more wavelengths within the 460 to 523 nm range and then fitting a parabolic curve to the measured values. As an example, spectra from hemoglobin samples could be tested using three wavelengths to perform a fit and determine the minima, such as 474 nm, 488 nm, and 506 nm. Example 1 below provides a detailed example of a possible minima determination technique. Note, there is no calibration of data required to account for changes in path length, hemoglobin concentration, or pH (at least for pH's from 6.6-7.4), thereby making this aspect of the present invention more user friendly than some prior techniques. Further, the potential use of the minima to determine oxygen saturation in scattering systems (cellular) is intriguing because the spectral minima is not significantly changed by scattering.

The oxygen saturation of the sample varies linearly with the location of the minimum from the optical density vs. wavelength parabolic curve. Referring to FIG. 1*a*, the different samples of hemoglobin have a minimum that moves from about 480 nm at low oxygen saturations to about 510 nm at high oxygen saturations. Thus, oxygen saturation may be accurately calculated based upon optical density measurements of any given sample at least three wavelengths between about 460 and 523 nm, followed by the determination of the local minimum and the calculation of the oxygen saturation based on the linear relationship of the wavelength at which the local minimum occurs and the oxygen saturation value. Thus, oxygen saturation ($S_{O2}$), in percent, may be determined as the measured minimum in nm ($\lambda$) minus the minimum at a saturation of 0% ($\lambda_0 \approx 478$ nm) divided by the minimum at a saturation of 100% ($\lambda_{100} \approx 510$ nm) minus the minimum at a saturation of 0% ($\lambda_0 \approx 478$ nm). Thus the oxyhemoglobin saturation of free hemoglobin or hemoglobin in blood can be calculated using the equation:

$$S_{O2}=100(\lambda-\lambda_0)/(\lambda_{100}-\lambda_0),$$

for a typical calculation for the data shown, $S_{O2}=100(\lambda-478 \text{ nm})/(33 \text{ nm})$.

The appropriate values of $\lambda_{100}$ and $\lambda_0$ will vary with the method for determining the minimum. Some other methods for generating a fit to these minima include the use of hyperbolic models, using the best fit to the whole spectra to determine the minima and using the changing slope in the region.

The accuracy of this method applies to hemoglobin and whole blood samples in vivo and in vitro. In this regard, tests were performed using these calculated minima to measure oxygen saturation in scattering blood samples when pH, path length and blood oxygen saturation were varied. The minima moved across the spectra in a similar manner to that seen in hemoglobin. The fit of the minima to saturation was calibrated and accurate to ±3.9% saturation. In addition to the minima fit, it was noted that the scattering created significant variations in the shape of the spectra without changing the minima.

Note that it is a simple matter to measure this same spectral component as a spectral maximum in transmission as transmission is the inverse antilog of the optical density. That is, optical density O.D.=−Log(transmission) or simply transposing Transmission=$10^{-(O.D.)}$ making the use of a transmission maximum or a rapid slope change in optical density or transmission in this region of the optical spectrum a trivial adaptation of this method that is claimed by reference.

The above analysis for determining the minima of a parabola relied upon the real portion of the root of the parabolic fit equation to measure the absorptive component of the blood (hemoglobin saturation). According to a second embodiment that relies upon the imaginary portion of the root of the parabolic fit equation, the hematocrit of a sample may be determined from optical density measurements at the three or more wavelengths with the light traveling a known path length. In this regard, the imaginary component of the root of parabola that is best fit to the optical density determined at three wavelengths (as described above) is dependant on hematocrit and path length. When the oxyhemoglobin saturation is held constant (such as at a high value found in arterial blood between 94% and 100%) and the path length is known, the change in hematocrit is inversely proportional to the increase in the imaginary root of the parabolic fit equation.

As explained below, the imaginary portion of the root, that is, the square root of the ratio C/A, is used to measure the hematocrit of the blood. The B/(2*A)+square root of (C/A), where A, B, and C are the parabolic best fit coefficients (see Example 1 for a method of calculating A, B, and C), at high saturation for hemoglobin is found to be equal to a constant D for any given oxygen saturation. Subtracting the Hgb root, i.e. −B/(2*A), from the blood root, i.e. Sqrt(C/A), gives the equation:

$$B/(2*A)+(\text{square root of }(C/A))-D=SC \text{ wherein SC is the blood scattering coefficient.}$$

1/SC linearly corresponds to the hematocrit for any given path length of the light through the blood in forward transmission. Thus, a system using this technique would require that the light travel in the forward direction through a fixed pathlength to a detector. Reasonable pathlengths are approximately 25 to 300 microns, more preferably 100 to 200 micron pathlengths.

Thus, the SC for blood may be determined by using three or more wavelengths to determine the coefficients A, B and C. These components, along with the measured path length are used to determine both the oxygen saturation of the blood, the value of the constants D, SC, and subsequently, the hematocrit. The path length is not required for measuring the oxyhemoglobin saturation of the blood, but is required for determining the hematocrit. Furthermore, the system that attempts to measure hematocrit using this technique must measure the optical density in the forward direction. Systems that do not attempt to measure the hematocrit do not have the restriction and can measure oxygen saturation by measuring the minima in backscattered or forward scattered signals without regard to pathlength.

In order to implement the foregoing methods of oxygen saturation and hematocrit determination, various devices may be employed. An application of this technology that is foreseen is the use of this technique to develop a calibrated intravenous or intra-arterial fiber optic catheter. This catheter uses an optical fiber to deliver the interrogating light signal to the blood and to detect the reflected signal which will then be analyzed to determine the oxyhemoglobin saturation and/or the hematocrit. In one embodiment, the device may consist of a fiber optic catheter, a laser light source or sources producing light having at least three wavelengths in the spectral range from 460 nm to 523 nm, a detector for power output from the source to the catheter tip and a detector for the return signal. This device may measure the ratio of the total signal provided to the blood (Io) and the total signal reflected by the blood (Ir). This ratio Ir/Io will correspond to the transmission (T). The optical density (O.D.) of the blood used for the analysis described above will be defined by the equation:

$$O.D.=-\log(T)=-\log(Ir/Io)$$

According to a variation of this embodiment, the hematocrit determination is accomplished with a dual fiber catheter with the tips aimed at each other, with a gap of 100-200 microns and blood flowing between them. Other systems may be used such as prisms that bend the light at the detector or the source in order to have the same effect.

The parabolic fit to at least three of these optical densities for a given measurement will be used to determine the minima and thus the saturation. When the catheter tips are aimed at each other then the same technique can be used to measure the minima as well as the other roots for hematocrit as described above.

According to another embodiment of the invention, where the light is delivered to the back of the eye as a collimated beam that is scattered by the layers of the retina, the thickness of a retinal layers may be measured by using information conveyed by the lateral intensity distribution of the light reflected back to the detector during spectroscopic analysis. Measured thickness may be compared to standard thicknesses in order to determine if the retinal layer(s) is abnormal. A practical application of this test is the detection of macular degeneration.

According to this embodiment, a small spot on the retina (about 30 to 120 microns in diameter) is illuminated using one or more wavelengths of light. The spatial distribution of the scattered and reflected light returning to the detector is measured. An exemplary method of obtaining the return signal is shown in Example 2 below. Advantageously, the retina is scanned and data is obtained point-by-point across the surface of the retina while the interrogating spot remains stationary.

Referring to FIG. 3, a particular spot on the surface of the retina is illuminated. A portion of the light is returned in the form of directly reflected backscatter from the illuminated spot and another portion is returned in the form of diffused light that is laterally scattered by the different layers of the retina. Referring to FIG. 4, the illuminance distribution of a scanned spot contains information of return illuminance (optical flux) vs. the position on the retina from which the light returned. The distribution curve is represented by a gradually sloping hill having a distinct intermediate peak. The directly reflected component (indicated as range 30 in FIG. 4) of the curve is eliminated from consideration so that the scattered component of the curve may be analyzed since this portion of the curve is predominantly based on light that has propagated through and been scattered by the retina. One possible change the distribution of scattered light would be seen when the layers of the retina are thinned (as in Macular degeneration) leading to less lateral scattering of light and a more pronounced intermediate peak. The directly reflected component may be separated from the remainder of the curve by various techniques such as by defining the directly reflected component to be that region within one half of the central peak intensity. One method for standardization between individuals analyzing would embody measurement of the total return signal and normalization of the measurement at each pixel (pixel return flux/total return flux).

It has been found that lasers producing light within the visible red region are advantageously used for illumination of multiple layers of tissue as envisioned in this embodiment. Red lasers provide a readily discernable spatial distribution upon reflection. Further, the red laser is advantageous because it may simultaneously be used as a tracking or targeting laser while providing spectroscopic data for use in determining retinal layer(s) thickness.

This method may therefore be used to measure tissue layer thickness as well as cellular scattering property changes which are not limited to the retina but may be used for evaluation of any optically accessible tissue. One anticipated use for this method is to indicate the potential for or onset of macular degeneration. Further, by repeated measurements over time, degeneration of the retinal thickness may be monitored.

Each of the foregoing methods may be implemented on a pixel-by-pixel basis in which laser(s) of the desired wavelength(s) illuminate the retina, pixel-by-pixel. The spectroscopic information of each pixel is analyzed in accordance with the above described techniques. In order to isolate a retinal vessel, the spectroscopic information for each pixel may be compared to that of the adjacent pixels. Using a nearest neighbor or other conventional approach, regions of the retina are categorized and mapped. Regions of the mapped retina that return spectroscopic data corresponding to known characteristics of retinal vessels are then known to be vessels and subject to subsequent analysis according to the embodiments above.

EXAMPLES

Example 1

Determination of a Local Minima from Optical Density Measurements with at Least Three Wavelengths The parabolic minimum of optical density measure against wavelength may be determined using the following method with three wavelengths:

$$OD = A*X^2 + B*X + C \qquad (eq. 1)$$

wherein OD is the total optical density of the sample; A, B, and C are constants unique to the given spectra; and X is the wavelength of the interrogating light source OD is measured at each of three chosen wavelengths within the 460 to 523 nm range and the three constants A, B, and C are determined from the equations resulting from the three wavelengths (three equations, three unknowns).

Taking the derivative of the above equation (eq. 1) gives the equation:

$$d(OD)/dx = 2AX + B \qquad (eq. 2)$$

Identifying the minima for this equation where the derivative is zero gives the equation:

$$0 = 2AX + B, \qquad (eq. 3)$$

Solving for X, the wavelength where the optical density in this region is minimal gives the equation:

$$X = -B/(2A) \qquad (eq. 4)$$

Thus, the applicable minima for a given sample or subject may be easily determined from OD measurements at three or more wavelengths.

Example 2

Detection of a Flux Illuminance Distribution

This exemplary method allows the quantification of scattered light exiting an eye, which yields a complete measurement of the optical diffused light and the absorptive differences between surface and underlying structure.

The main components of the device's optical system (FIG. 2) consist of a (a) tracking laser input path—L1, (b) detector—D, (c) confocal partial filter—SF, (d) beam splitter/combiner for D and L1 paths—BS1, (e) scanning system #1—SS1, (f) scanning system #2—SS2, (g) relay optics for conjugating SS1 & SS2—RO (h) probe lasers input path—L2, (i) beam splitter/combiner for D and L2 paths—BS2, and (j) objective lens—O.

The objective lens, O, collimates the light from either source path L1 or L2 and directs it into the eye. In addition, O also makes conjugate the scanning system SS2 to the pupil of the eye. Motion of the scanning system SS2 scans the probe beam L2 across the back of the retina of the eye. SS2 also de-scans the light that exits from the pupil of the eye along the input axis. The beam splitter/combiner BS2 combines and co-aligns the D and L1 optical paths. Depending on the application, desired contrast, and the scattering properties, BS1 and BS2 may be either polarizing or non-polarizing beam splitters. The relay optics RO conjugates the two scanning systems SS1 and SS2. The scanning system SS1 scans and de-scans the source L1 and the confocal detection path across the retina relative to but independent of the scanned source 2. Light from source 2 directed into the eye is focused and illuminates a single spot (~40 microns in diameter) that SS2 scans across the retina. A small proportion of light is directly reflected while the rest of the light penetrates and scatters in the retinal tissue layers. Some of the scattered light re-emerges from the retina and exits back out the eye through the pupil where it can then be detected. The spot area over which this light emerges is much larger than the initial small spot. FIG. 4 illustrates the cross-section of exemplary exitance of the reflected and scattered light. Note that the distribution consists of two parts, a central directly reflected peak and a broad diffusely scattered base.

Example 3

Derivation of Improved Method of Oxygen Saturation Measurement

As noted above, oximetry equations used in the prior art typically assume that there are only two forms of hemoglobin, deoxyhemoglobin and oxyhemoglobin. However, hemoglobin exists as a four molecule grouping that binds to oxygen cooperatively with at least 10 different intermediate combinations of oxygen, hemoglobin and macromolecular structures. In order to more closely model the spectral response of hemoglobin in blood the equilibrium equations for the different oxyhemoglobin intermediates were analyzed. Because hemoglobin has four binding sites that cooperatively bind to oxygen, the resulting equilibrium equations to characterize this relationship were used. Using the equation for oxyhemoglobin saturation $S=(((Po_2^3+150\ Po_2)^{-1}\times23,400)+1)^{-1}$ the oxyhemoglobin saturation curve was generated. Using the four equilibrium relationships, the equation for saturation $S=(0.25C1+0.5C2+0.75C3+C4)/(C0+C1+C2+C3+C4)$, (C0-C4 are hemoglobin bound to 0-4 oxygen molecules) and the data from the oxyhemoglobin disassociation curve, the relative contributions of C0 through C4 were regressed. It was determined that the relative contribution of C1 and C2 are both higher than C0 at high saturations and that at low saturations the contribution of C1 is significantly higher than C4.

To further characterize this effect, a series of hemoglobin samples from fresh packed human red blood cells obtained using an IRB approved protocol were generated. The hemoglobin solutions were then set to various oxyhemoglobin saturations. A Cary 100 Spectrophotometer was used to measure the transmission in the forward direction across the 450-850 nm waveband at 2 nm increments for samples at thicknesses of 100 or 200 microns using hemoglobin concentrations from 32 g/DL to 4.5 g/DL and at a pH of 6.6-7.4.

The total variance of the optical density was measured at each wavelength as oxyhemoglobin saturation was varied and the reported isobestic points were found to be variant. Note that the isobestic points are expected to have a variance of near zero.

The optical density was not linear at fixed values of diameter and concentration for certain wavelength bands. This effect is pronounced for wavelengths above 670 nm.

A three wavelength model equation was used to solve for oxygen saturation using the optical densities of the blood obtained from the spectrophotometer at wavelengths optimized based on a conventional approach in the form of a previously published spectra and found that the saturation obtained was accurate but not well calibrated (error was +−14% S.D.). Further, a conventional two wavelength saturation model equation was used to analyze the data and it was found that the oxyhemoglobin saturation was accurate to ±4-13% depending on the wavelength combination selected.

As noted above, the spectra of the hemoglobin in the 460-523 nm range has a minimum that moves across the waveband in this region from about 510 nm at high oxygen saturations to about 480 nm at low oxygen saturations. No other spectral components in the visible light range move laterally across the spectrum so dramatically. The largest similar change elsewhere is about 6 nm in width. Indeed, most of the spectral characteristics simply change in amplitude as oxygen saturation changes.

The spectra from all the hemoglobin samples tested were analyzed using three wavelengths to perform a fit and determine the minima (474 nm, 488 nm, and 506 nm). There was no calibration of data to account for changes in pathlength (100 microns and 200 microns), [Hgb], or pH. When the minimum was used to calculate the saturation in accordance with one aspect of the present invention, the standard deviation of the residuals was ±3.0% saturation.

The results of the hemoglobin model analysis, along with similar analysis using ten intermediates with similar findings, bring into doubt the assumption made in oximetry that oxyhemoglobin saturation is a simple ratio of the spectral contributions of C0 and C4 alone. Since the energy states of these molecules are known to be significantly different from each other, it seems unlikely that the optical characteristics of the intermediates is a simple weighted average of the relative concentrations of oxyhemoglobin and deoxyhemoglobin in the sample. The spectral analysis of intermediately saturated oxyhemoglobin solutions supports this concern since the predicted isobestic points and the linear responses to changes in saturation are not well preserved at all wavelengths. Furthermore, reports in the literature using the red to near infrared spectra for the determination of blood and hemoglobin pH independent of oxygen saturation also supports this conclusion.

The use of the spectral minima in the blue green region described here is intriguing because such a narrow waveband is expected to decrease unknown spectral variance seen when in vivo testing is performed and this waveband is in one of the most oxygen sensitive areas of the spectrum. The use of the blue minimum to determine oxygen saturation of hemoglobin was more accurate and better calibrated than any combination of two wavelengths tested. In this system, the blue minima technique did not require the measurement of the path length, the concentration or the pH. All of these parameters are important if the classical approach to oximetry is used.

The embodiments of this invention can be used to measure the arterial venous oxygen saturation difference, an essential component required for measuring the autoregulatory state of the retina.

The output of a detector can be analyzed by a computer program product as generally described by U.S. Pat. Nos. 5,776,060 and 5,935,076, the contents of which have been incorporated herein. As will be apparent to those of skill in the art, the computer program instructions of a computer program product may be executed by a processing element, such as a microprocessor, integrated circuit or other computing device. It should therefore be understood that the various determinations and the analyses described above can be implemented by computer program instructions. These computer program instructions may be loaded onto a processing element or other programmable apparatus to produce a machine, such that the instructions which execute on the computer or other programmable apparatus create means for implementing the functions described above. These computer program instructions may also be stored in a computer-readable memory that can direct a computer or other programmable apparatus to function in a particular manner, such that the instructions stored in the computer-readable memory produce an article of manufacture including instruction means which implement the functions specified above. The computer program instructions may also be loaded onto a processing element or other programmable apparatus to produce a computer implemented process such that the instructions which execute on the computer or other programmable apparatus provide steps for implementing the functions specified above.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device for determining the oxygen saturation of blood, the device comprising a light source for illuminating blood with at least three distinct wavelengths ($\lambda$) of light, each within the range of about 460 nm and 523 nm; and a processing element configured to determine optical density of the blood sample at each of the at least three wavelengths and to determine a parabolic function based on the correspondence of measured optical density to the respective wavelengths said processing element also configured to determine the minimum wavelength ($\lambda_{min}$) that corresponds to an inflection point of the parabolic function, and said processing element further configured to correspond the determined minimum wavelength ($\lambda_{min}$) to an oxygen saturation concentration of the blood.

2. A method for determining the oxygen saturation of blood, comprising the steps of:

providing a device according to claim 1;

illuminating blood with at least three distinct wavelengths ($\lambda$) of light, each within the range of about 460 nm and 523 nm;

measuring optical density of the blood sample at each of the at least three wavelengths;

determining a parabolic function based on the correspondence of measured optical density to the respective wavelengths;

determining the minimum wavelength ($\lambda_{min}$) that corresponds to an inflection point of the parabolic function; and, corresponding the determined minimum wavelength ($\lambda_{min}$) to an oxygen saturation concentration of the blood.

3. The method of claim 2, wherein the blood is illuminated in vitro or in vivo.

* * * * *